(12) United States Patent
Jepsen et al.

(10) Patent No.: US 10,195,069 B2
(45) Date of Patent: Feb. 5, 2019

(54) OUTLET FOR A UROSTOMY APPLIANCE

(71) Applicant: Coloplast A/S, Humlebaek (DK)

(72) Inventors: Erik Lund Jepsen, Vaerloese (DK); Kamilla Grove Sund, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 15/325,935

(22) PCT Filed: Jul. 10, 2015

(86) PCT No.: PCT/DK2015/050211
§ 371 (c)(1),
(2) Date: Jan. 12, 2017

(87) PCT Pub. No.: WO2016/008493
PCT Pub. Date: Jan. 21, 2016

(65) Prior Publication Data
US 2017/0156919 A1 Jun. 8, 2017

(30) Foreign Application Priority Data
Jul. 16, 2014 (DK) .................................. 2014 00386

(51) Int. Cl.
*A61F 5/44* (2006.01)
*F16L 37/413* (2006.01)
*F16K 31/528* (2006.01)
*A61M 39/24* (2006.01)

(52) U.S. Cl.
CPC .......... *A61F 5/4405* (2013.01); *F16K 31/528* (2013.01); *F16L 37/413* (2013.01); *A61M 2039/2486* (2013.01)

(58) Field of Classification Search
CPC ........ A61F 5/4405; A61F 5/44; F16K 31/528; F16K 31/50; F16K 31/504; F16K 1/04; F16L 29/02; F16L 37/413
USPC ....................................................... 251/149.5
See application file for complete search history.

(56) References Cited

U.S. PATENT DOCUMENTS

| 1,022,759 | A | * | 4/1912 | Steiner | ................... | F16L 37/252 |
| | | | | | | 285/361 |
| 1,968,075 | A | * | 7/1934 | Ewald | ................... | F16L 37/252 |
| | | | | | | 251/149.5 |
| 2,248,701 | A | * | 7/1941 | Fowler | ................... | F16L 37/107 |
| | | | | | | 251/149.5 |

(Continued)

FOREIGN PATENT DOCUMENTS

| EP | 1800632 A1 | * | 6/2007 | ........... | A61F 5/4405 |
| GB | 2092690 A | * | 8/1982 | ........... | A61F 5/4405 |

(Continued)

*Primary Examiner* — Reinaldo Sanchez-Medina
*Assistant Examiner* — David Colon Morales
(74) *Attorney, Agent, or Firm* — Coloplast Corp., Coloplast A/S; Nick Baumann

(57) ABSTRACT

An outlet (4) for a pouch (1) in a urostomy appliance is provided. The outlet has a valve with a valve housing (5) and a valve stem (6) that is movable in the longitudinal direction with respect to the valve housing. In a position of the valve stem, the stem can freely rotate with respect to the valve housing, so as to prevent kink and obstructions in a tube connecting the valve with a collecting bag. A urostomy appliance with an outlet is also provided.

7 Claims, 3 Drawing Sheets

(56) References Cited

U.S. PATENT DOCUMENTS

| | | | |
|---|---|---|---|
| RE26,674 E  * | 9/1969 | Ilg | A61M 3/0245 |
| | | | 222/570 |
| 3,476,138 A | 11/1969 | Doremus et al. | |
| 4,055,179 A | 10/1977 | Manschot et al. | |
| 4,306,743 A  * | 12/1981 | Hinshaw | F16L 37/248 |
| | | | 285/260 |
| 4,603,837 A  * | 8/1986 | Steer | F16K 5/04 |
| | | | 251/345 |
| 4,931,044 A  * | 6/1990 | Beiter | A61B 5/15003 |
| | | | 251/149 |
| 5,071,413 A  * | 12/1991 | Utterberg | A61M 5/162 |
| | | | 604/411 |
| 5,135,199 A | 8/1992 | Cross et al. | |
| 5,156,603 A  * | 10/1992 | Olsen | A61F 5/4405 |
| | | | 251/341 |
| 5,226,564 A  * | 7/1993 | Steer | A61F 5/4404 |
| | | | 222/107 |
| 5,330,154 A  * | 7/1994 | Mashburn | F16L 37/248 |
| | | | 251/144 |
| 5,509,911 A | 4/1996 | Cottone et al. | |
| 6,032,926 A  * | 3/2000 | Fuchs | A61J 1/10 |
| | | | 251/149.1 |
| 6,132,407 A | 10/2000 | Genese et al. | |
| 6,156,025 A  * | 12/2000 | Niedospial, Jr. | A61J 1/1412 |
| | | | 604/408 |
| 6,902,146 B1 * | 6/2005 | Elliott | A61F 5/4405 |
| | | | 251/351 |
| 7,681,764 B2 * | 3/2010 | Nini | B67D 3/045 |
| | | | 222/153.05 |
| 8,070,736 B2 * | 12/2011 | Nishtala | A61M 39/10 |
| | | | 604/328 |
| 8,088,114 B1 | 1/2012 | Pauze | |
| 2006/0189961 A1* | 8/2006 | Miyahara | A61M 39/14 |
| | | | 604/535 |
| 2008/0287919 A1* | 11/2008 | Kimball | A61M 25/1011 |
| | | | 604/533 |
| 2012/0130329 A1 | 5/2012 | March et al. | |
| 2013/0338616 A1* | 12/2013 | Galindo | A61F 5/4405 |
| | | | 604/335 |

FOREIGN PATENT DOCUMENTS

| | | |
|---|---|---|
| GB | 2125130 A1 | 2/1984 |
| WO | 9945866 A1 | 9/1999 |
| WO | 0102283 A1 | 1/2001 |

* cited by examiner

OUTLET FOR A UROSTOMY APPLIANCE

The invention relates to an outlet with a valve for a urostomy appliance with means for providing free rotation between the valve and a tube connecting the urostomy appliance to a collecting bag.

SUMMARY OF THE INVENTION

The invention relates to an outlet for a urostomy pouch, the outlet including a valve. This valve has a valve housing and a valve stem that is movable in the longitudinal direction with respect to the valve housing. The valve stem has a position in which the valve stem is able to rotate freely with respect to the valve housing. During the night, the user may decide to connect a collecting bag through a tube to the urostomy pouch so that urine can be collected in the collecting bag. The free rotation of the valve stem with respect to the valve housing substantially prevents kinking of the connecting tube between the collecting bag and the urostomy pouch. Thereby free flow between the urostomy pouch and the collecting bag is ensured.

DETAILED DESCRIPTION OF THE INVENTION

Figure 1:
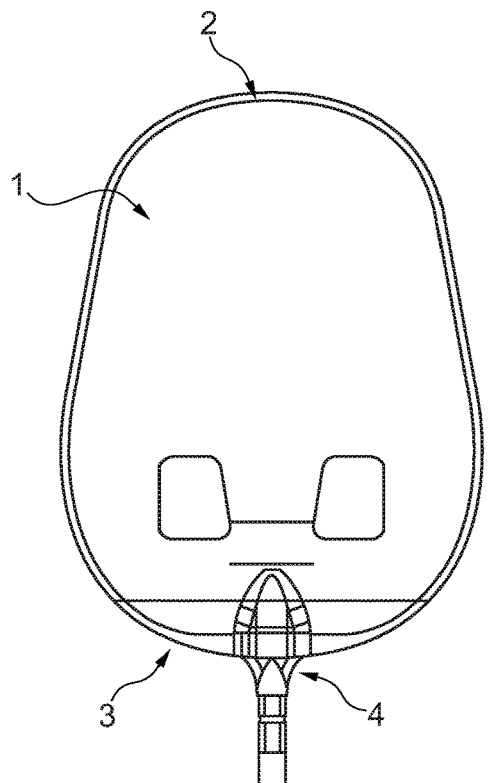
FIG. 1 illustrates a front view of a urostomy pouch according to an embodiment of the invention.
Figure 2:
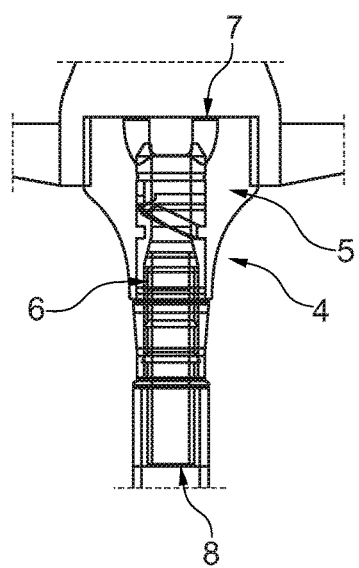
FIG. 2 illustrates a detailed cross-sectional view of an outlet including a valve according to an embodiment of the invention.
Figure 3:
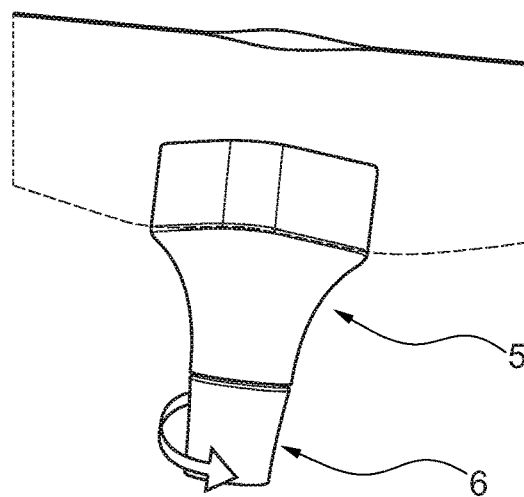
FIGS. 3 and 4 illustrate the function of the valve.

A urostomy appliance is typically used to collect urine from a urostomy connecting the urine system in the body with the abdominal surface of the user. The appliance is directly or indirectly adhered to the skin of the user around the urostomy. Urostomy appliances includes a collecting pouch for collecting the urine. The pouch is typically provided with an outlet including a valve at the bottom of it making it possible for the user to drain the urine into a suitable place during the day—e.g. a toilet. At night, a tube for a collecting bag may be connected to the valve. However, such a tube is prone to kinking and thereby the flow of urine between the pouch of the urostomy appliance and the collecting bag is obstructed. This may lead to leakage of urine from the urostomy appliance.

Known solutions include connectors with additional tubes to provide means for preventing kink of the tubing. However, there is still a need for a more convenient solution for the user.

Embodiments relates to an outlet for a pouch in a urostomy appliance comprising a valve with a valve housing and a valve seat in the proximal end of the valve housing cooperating with a stem positioned inside the valve housing, the valve having a closed position where the stem seals against the valve seat and an open position where the stem does not seal against the valve seat, wherein the valve in the open position has means for providing free rotation of the stem with respect to the valve housing.

An outlet with a valve as described above has the advantage that the stem may rotate freely with respect to the valve housing—and thus with respect to the attachment of the outlet to the pouch. This means that when the outlet of the pouch is attached to a tube for connecting the pouch to a collecting bag, the pouch will be able to rotate freely with respect to the tube—and thus eliminate (or at least largely reduce) the risk of kinking of the tube. Kinking of the tube may lead to leakage of the urostomy pouch—either at the outlet or at the attachment of the pouch to the abdominal surface of the user.

Whenever referring to the proximal end of the valve, the referral is to the end closest to the collecting pouch. Likewise, whenever referring to the distal end of the valve, the referral is to the end furthest away from the collecting pouch.

The axial direction is defined as the longitudinal direction of the valve.

A urostomy appliance is well-known in the art. The collecting pouch usually comprises a front wall on the distal side and a rear wall on the proximal side. The walls are made of gas and liquid impermeable foil material (for example of polyethylene (PE), polyvinyl-chloride (PVC) or ethylene-vinyl-acetate (EVA)) that is welded around the edges or the rim so as to form a pouch defining a collection chamber. The pouch includes a valve for leading out urine at the bottom of the pouch. The inlet opening is provided in the rear wall and placed in the upper part of the collecting pouch so that when a user stands up, the inlet opening will be above the midline of the collecting pouch. This leaves a larger collecting volume below the inlet opening. Thus, the top of the collecting pouch is defined as the part closest to the inlet opening, and the bottom is defined as the opposite part. Urostomy pouches are typically provided with an outlet at the bottom of the pouch that in its simplest form is an outlet closed by a detachable closure.

The valve used in the outlet of this invention is a type of valve that is well-known in the art of valves, such as a globe valve, gate valve or poppet valve. It includes a stem that is movable in the longitudinal direction of the valve with respect to a housing. When the stem is in one extreme position (in respect of this present valve, in the extreme proximal position), the proximal end of the stem will seal against a valve seat in a valve housing, usually through sealing means, also well-known in the art.

The parts of the valve may be made of e.g. a polyolefin material such as poly-ethylene. The sealing means may be made of LDPE.

In an embodiment of the invention, the valve includes bayonet coupling means for moving the stem along the housing of the valve. A bayonet coupling allows the user to simply twist the valve and move the valve between the open and closed position.

The bayonet coupling means may be in the form of a recess with a pitch on one of the valve housing or the valve stem cooperating with one or more protrusions on the other of the valve housing or the valve stem.

In an embodiment, the valve stem has a recess with a pitch on an outer surface of the stem cooperating with one or more protrusions in the valve housing for moving the stem in the proximal direction towards the valve seat, wherein the recess ends in an annular recess towards the proximal end of the valve.

When the user moves the stem in the distal direction with respect to the housing (e.g. by rotating), the stem will reach a point where an annular recess proximal on the stem will reach a protrusion on the housing. Cooperation between those two means that the stem can rotate freely with respect to the housing.

When the user wants to close the valve again, a simple movement of the stem in the proximal direction of the valve, perhaps combined with a rotation in a bayonet coupling, will allow the stem to enter into sealing closure with the housing.

In an embodiment of the invention, the bayonet coupling means include bumps towards the distal end indicating that the point of free rotation is reached.

In another embodiment, the bayonet coupling means include bumps towards the proximal end indicating that the point of closure is reached.

Embodiments relate to a urostomy appliance comprising a collecting pouch with a front wall and a rear wall, which are sealed together along the edges, and means for attaching the urostomy appliance to the user, the urostomy appliance further comprising an outlet as described above at a bottom of the urostomy appliance.

The means for attaching the urostomy appliance to the user may include a base plate for attaching to the skin of the user and a wafer on the urostomy appliance for coupling the appliance to the base plate. Alternatively, the appliance may include a wafer that is adapted for directly adhering it to the skin of the user.

DETAILED DESCRIPTION OF THE DRAWING

FIG. 1 illustrates a front view of a urostomy collecting pouch 1 with an outlet according to an embodiment. The pouch 1, includes a front wall and a rear wall (not shown) with a top 2 and a bottom 3. The outlet 4 is positioned toward the bottom 3.

FIGS. 2-5 illustrate in more detail the outlet 4 of a urostomy collecting pouch according to an embodiment. The outlet 4 includes a valve with a valve housing 5 and a valve stem 6 that is movable in the longitudinal direction of the valve. The valve seat 7 is in the proximal part of the valve between the proximal end of the valve stem 6 and the valve housing 5. In the distal end of the valve stem, the stem provides a cavity 8 for a connector to a tubing. In the embodiment shown, the movement in the longitudinal direction is done through a bayonet coupling comprising a recess 9 with a pitch on the valve stem 6 in cooperation with protrusions 10 at an inner surface of the valve housing 5. The valve stem 6 further includes an annular recess 11 towards the proximal end of the valve stem. In use, the user opens the valve by twisting the valve stem counter-clockwise (seen from the distal end of the valve), until the pitched recess 9 ends and the protrusions 10 enter into the annular recess 11. When the protrusions are in the annular recess 11, the valve stem can rotate freely with respect to the housing.

The embodiment of FIGS. 2 to 5 further includes that the pitched recess 9 has two minor bumps 12, 13—a proximal bump 12 towards the proximal end, just distally of the annular recess and a distal bump 13 towards the distal end of the recess just proximally of the distal end of the recess. These bumps are there to provide tactile feedback to the user of the position of the valve stem with respect to the housing. For example, when the user feels the proximal bump 12 during twisting of the valve stem, the user will know that the annular recess has been reached and that the valve is able to rotate freely. Likewise, when the user feels the distal bump 13 during twisting of the valve stem, the user will know that the valve is close to being closed.

Figure 4:
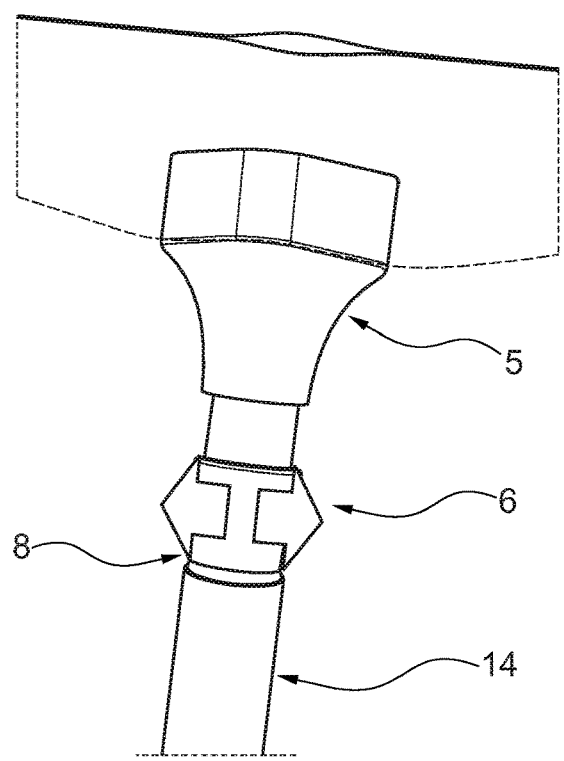
Figure 5:
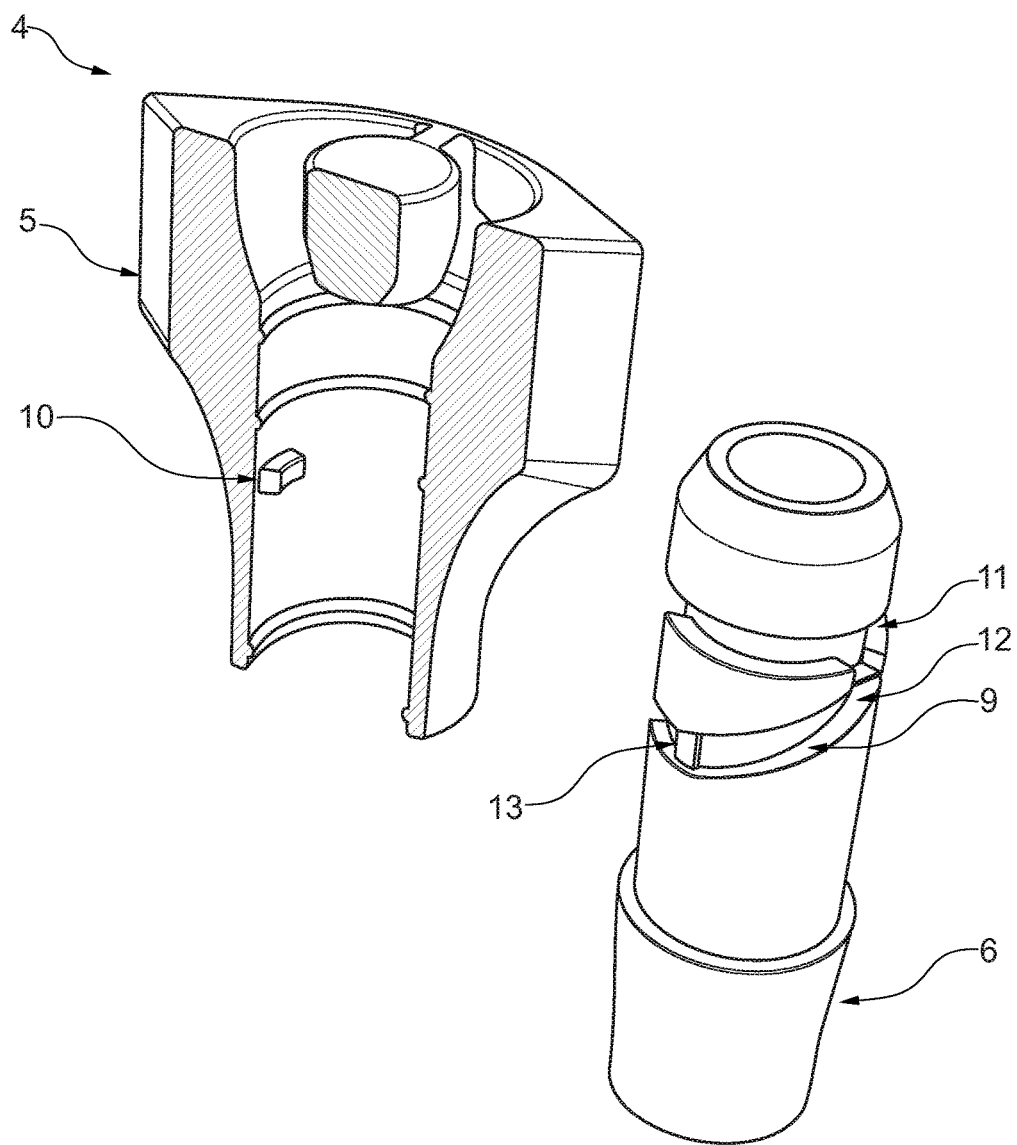
FIG. 5 illustrates an exploded view of the valve housing and the valve stem according to an embodiment of the invention.

FIG. 4 also illustrates a connector and tube 14 connected to the cavity 8 of the valve stem.

The invention claimed is:

1. An outlet for a pouch in a urostomy appliance, the outlet comprising:
    a valve housing forming a cavity, the cavity including a protrusion projecting from a wall of the cavity and the valve housing having a valve seat provided in a proximal end of the cavity;
    a valve stem positioned inside the cavity of the valve housing, the valve stem has a pitched recess with a non-zero pitch formed in an outer surface of the valve stem, the pitched recess is engaged with the protrusion in the valve housing, where the pitched recess extends to and intersects with a distal wall of an annular recess that is formed in the outer surface of the valve stem proximal of the pitched recess where the annular recess has a proximal wall spaced apart from the distal wall by a distance that is sized to receive the protrusion projecting from the wall of the cavity of the valve housing;
    wherein the outlet has a closed position where the valve stem seals against the valve seat and an open position where the valve stem does not seal against the valve seat, and wherein, when the protrusion is engaged between the distal wall and the proximal wall of the annular recess, the valve stem is retained in the valve housing and rotates freely relative to the valve housing.

2. The outlet of claim 1, wherein the pitched recess has a distal bump formed in a distal end of the pitched recess and adapted to provide a tactile feedback to a user.

3. The outlet of claim 1, wherein the pitched recess has a proximal bump formed in a proximal end of the pitched recess to provide a tactile feedback to a user.

4. The outlet of claim 1, wherein the pouch of the urostomy appliance has a rear wall sealed to a front wall to form a container, and the outlet is sealed to the front wall and to the rear wall at a bottom of the pouch.

5. The outlet of claim 1, wherein in the closed position, the protrusion is engaged with the pitched recess to retain the valve stem in sealed engagement with the valve seat.

6. The outlet of claim 1, wherein in the closed position, the pitched recess includes a bump to indicate closure of the outlet whereby the protrusion is engaged with the pitched recess to retain the valve stem in sealed engagement with the valve seat.

7. The outlet of claim 1, wherein the valve housing of the outlet is sealed to the pouch of the urostomy appliance, with the outlet further comprising:
    a tube connected to the valve stem; and
    a collecting bag connected to the tube;
    wherein, in the open position, where the protrusion moves within the annular recess to allow free rotation of the valve stem relative to the valve housing to substantially prevent kinking of the tube connected to the valve stem.

* * * * *